United States Patent
Salerno

(10) Patent No.: US 9,476,079 B2
(45) Date of Patent: Oct. 25, 2016

(54) METHODS TO MUTATE CIRCULAR DEOXYRIBONUCLEOTIDES

(71) Applicant: KENNESAW STATE UNIVERSITY RESEARCH AND SERVICES FOUNDATION, Kennesaw, GA (US)

(72) Inventor: John C. Salerno, Acworth, GA (US)

(73) Assignee: KENNESAW STATE UNIVERSITY RESEARCH AND SERVICES FOUNDATION, INC., Kennesaw, GA (US)

( * ) Notice: Subject to any disclaimer, the term of this patent is extended or adjusted under 35 U.S.C. 154(b) by 177 days.

(21) Appl. No.: 14/372,692

(22) PCT Filed: Jan. 18, 2013

(86) PCT No.: PCT/US2013/237237
§ 371 (c)(1),
(2) Date: Jul. 16, 2014

(87) PCT Pub. No.: WO2013/109950
PCT Pub. Date: Jul. 25, 2013

(65) Prior Publication Data
US 2014/0363850 A1 Dec. 11, 2014

Related U.S. Application Data

(60) Provisional application No. 61/588,989, filed on Jan. 20, 2012.

(51) Int. Cl.
*C12P 19/34* (2006.01)
*C12Q 1/68* (2006.01)

(52) U.S. Cl.
CPC ............. *C12P 19/34* (2013.01); *C12Q 1/6844* (2013.01)

(58) Field of Classification Search
CPC .......... C12Q 1/6844; C12Q 2521/331; C12Q 2525/179; C12Q 2531/125; C12P 19/34
See application file for complete search history.

(56) References Cited

U.S. PATENT DOCUMENTS

| 5,932,419 A | 8/1999 | Bauer et al. |
| 2002/0083488 A1 | 6/2002 | Miyawaki |
| 2003/0032037 A1* | 2/2003 | Bauer .................. C12N 15/102 435/6.16 |
| 2006/0134624 A1 | 6/2006 | Salerno |

FOREIGN PATENT DOCUMENTS

| WO | 93/13216 A1 | 7/1993 |
| WO | 99/35821 A1 | 7/1999 |
| WO | 2005/040342 A2 | 5/2005 |
| WO | 2008/131580 A1 | 11/2008 |

OTHER PUBLICATIONS

International Search Report PCT/US2013/022237, mailed May 15, 2013 (4 pages).
Written Opinion PCT/US2013/022237, mailed May 15, 2013 (5 pages).
Wang and Malcolm. Two-Stage PCR Protocol Allowing Introduction of Multiple Mutations, Deletions and Insertions Using QuikChange™ Site-Directed Mutagenesis. BioTechniques 26 (1999) 680-682.
Salerno et al. A Single-Stage Polymerase-Based Protocol for the Introduction of Deletions and Insertions Without Subcloning. Molecular Biotechnology 29 (2005) 225-232.
Roberts et al. REBASE: restriction enzymes and methyltransferases. Nucleic Acids Research 31 (2003) 418-420.
Erdogan et al. INSULT A Novel Mutagenesis Method Generating High Yields of Closed Circular Mutant DNA With One Primer Per Mutant. Molecular Biotechnology 30 (2005) 21-30.
Chen and Ruffner. Amplification of closed circular DNA *in vitro*. Nucleic Acids Research 26 (1998) 1126-1127.
Chung and Miller, A rapid and convenient method for the preparation and storage of competent bacterial cells. Nucleic Acid Research 16 (1988) 3580.

* cited by examiner

*Primary Examiner* — Cynthia B Wilder
(74) *Attorney, Agent, or Firm* — Thompson Hine LLP

(57) ABSTRACT

The invention provides improved mutagenic plasmids and a method for making and using them. In one embodiment a cyclic mutagenic nucleic acid is replicated to form interlocking, digestibly separable duplex or simplex rings; and then one or more of the interlocked rings are cleaved selectively by means of a restriction enzyme to liberate an intact duplex or simplex ring. The mutagenic plasmids show substantially improved efficiencies in transforming cellular microorganism that are exposed to them.

17 Claims, 7 Drawing Sheets

METHODS TO MUTATE CIRCULAR DEOXYRIBONUCLEOTIDES

RELATED APPLICATIONS

This is a National Phase of co-pending Application Serial No. PCT/US2013/022237 filed Jan. 18, 2013 which claims priority to U.S. Patent Application Ser. No. 61/588,989 filed Jan. 20, 2012, each of which is expressly incorporated by reference in its entirety.

Compositions and methods to produce closed circular double-stranded (ds) deoxyribonucleotide (DNA) species containing site-specific mutations, in high yield, are disclosed. The methods are useful to introduce one or more desired mutations into a gene-containing plasmid. The method uses a first mutagenic primer and a second primer that is non-complementary to the first primer. The method uses an enzyme, such as a selected restriction endonuclease, to untangle circular DNA. The resulting closed circular dsDNA species is substantially free of entanglements with other circular DNA species. Circular dsDNA provides higher transformation efficiencies than linear DNA. The method resulted in mutagenic circular DNA free of interfering DNA species, such as entangled circular DNA strands, that permitted higher efficiency transformation without the need to use ultracompetent cells. The method controlled creation and replication of mutagenic plasmids to substantially eliminate entanglements during in vitro production of the site-directed mutants. The resulting mutagenized plasmids had substantially eliminated entanglements, thus increasing cell transformation relative to mutant plasmids produced by current methods, i.e., they produce higher transformation efficiencies.

The polymerase chain reaction (PCR), widely used to amplify DNA, offers a replicatory cascade. Each new copy of a nucleic acid sequence can be a template for additional copies, and millions of copies can be made in a single reaction vessel from a single template molecule and low amounts of polymerase enzyme. The copies are used in numerous applications, e.g., sequencing, gene analysis, forensic identification, biological taxonomy, detecting and diagnosing genetic disorders, infectious diseases, etc.

During the PCR protocol, thermophile-derived polymerase enzymes and DNA are heated to nearly 100° C., typically 95° C., for several minutes to break the hydrogen bonds between the complementary paired strands, denaturing them to single strands. The reaction medium includes primers, i.e., oligonucleotides that closely complement a targeted region of DNA. The reaction temperature is decreased, typically from the higher temperature to 65° C. to 50° C. for about one minute so the separated DNA strands can anneal to the primers just below their melting and denaturation temperatures ($T_m$). Polymerase enzyme then docks on the primer-template duplex and initiates DNA synthesis. At its optimal polymerization temperature, about 70° C. to 80° C. inclusive, depending on the polymerase, the enzyme can extend the chain length by a thousand bases per minute. Many PCR variations exist for special purposes, working by the same principle.

Among these special purposes is site-directed mutagenesis, i.e., insertions, deletions, and base substitutions in genetic material. PCR and other polymerase based methods are favored for site-directed mutagenesis because they do not require ssDNA rescue, subcloning, or ligation.

Commercial kits, such as Strategene Quik-Change®, helped to expedite use of polymerase-based site-directed mutagenesis. Quik-Change® employed complementary mutagenic primers and paired linear DNA containing the entire sequence of the target gene and plasmid vector, forming duplexes along most of their length; primer-derived sequences extend from opposite ends of the duplex region, and provide large sticky ends that enable the duplex to cyclize into a transient, doubly nicked circular species. These products transform 'ultra-competent' cells provided by the manufacturer. Ultra competent cells, such as commercially available strains XL2 Blue and XL10 gold (Stratagene), have transformation efficiencies several orders higher than standard competent cells. Standard competent cells typically include calcium competent cells, such as DH5α, which have been rendered competent by the calcium method, as known in the art. Upon successful mutagenesis and transformation, the cells then produce large amounts of closed circular DNA containing the desired mutant. Parental (i.e., unmutated) strands are suppressed by digestion with dpn1.

That method had several disadvantages (Wang and Malcolm 1999 Biotechniques, 26:680). Mutations more extensive than one or two base changes caused the two primers to bind to one another more strongly than to the template. The authors suggested modifying Quik Change® by using a preliminary phase in which each primer type is reacted in a separate tube and a few copies made, to prevent the formation of primer duplexes, and to allow synthesis of full length DNA copies with exact complements to the primers. The two tubes were mixed after that phase and an additional 8-10 PCR cycles was performed.

That modification failed because Quik Change® orients the 3' ends of both primers outward as they bind to their linear copies (Salerno et al., Molecular Biotechnology, 2005, 29:225). Consequently these linear strands are not templates for further copies, so amplification rates are linear and there is no chain reaction; even mixing the separately replicated tubes after a preliminary phase gives no chain reaction. Strategene, aware that Quik Change® amplifies linearly, and not by in vitro chain reaction, points to its advantage of fewer errors.

Salerno noted that the Quik Change® process is compromised by duplex formation between templates across primer-derived regions were not blocked by primer binding, followed by polymerase extension. These duplexed linear copies are counterproductive: they have blunt ends (i.e., lack single stranded sticky ends at the ends of the duplex region) that cannot be cyclized even transiently. They also contain an extra copy of the primer sequence within the gene coding region, and hence code for inactive proteins. They can act as templates for runaway PCR, overwhelming the useful product. This process also occurs in the Wang and Malcom modified procedure. A remedy was to perform the entire polymerase reaction sequence in separate tubes with only one primer each, and to mix the tubes without allowing polymerase to operate in the combined system. This produces the desired linear product as the predominant species. Because linear duplexes are not ideal for transformation, ultra-competent cells are required.

Circular PCR offered a potentially better approach (Chen and Ruffner 1998 Nucleic Acids Res., 26(4):1126, corrected in *Nucleic Acids Res.,* 1998 26(23):1126; WO/1999/035281). Circular PCR in combination with a thermostable ligase and polymerase, in theory, produces many copies of closed circular DNA, and can, in principle, be used to produce mutants. Circular PCR kits used a ligase-polymerase combination. A drawback to circular PCR is that it never actually occurs. The highly topologically entangled circular DNA produced by this method cannot act as a template for continued copying and therefore, exponential production of product does not result.

The most widely used polymerase-based mutagenic method begins with a super-coiled wild type plasmid as the template, and with two synthetic complementary primers containing the desired mutation; the primers complement complementary strands of the vector. Following PCR amplification, Dpn 1 nuclease is typically introduced to digest the dAM-methylated wild type selectively: only the mutated, unmethylated plasmid remains.

INSULT™ (Erdogan et al., 2005, Molecular Biotechnology, 30(1): 2; U.S. Published Patent Application No. 2006/0134624) introduced an improved procedure with non-complementary primers. INSULT™ procedure begins with a double-stranded circular vector bearing the gene to be mutated; the vector is then denatured to obtain a closed-circle, single-stranded template. The template is hybridized with a single primer in a heteroduplex, which is amplified in incremental cycles; a thermophilic ligase is used to repair nicks after each cycle. The ligated products are denatured and their single strands are hybridized with a different primer for further copying and ligation. The latter primer can be generic (i.e., not mutagenic and capable of binding to any desired position in the plasmid/gene combination, and therefore, the same second primer can be used for many different mutants). The mutated double-stranded products are then used to transform bacterial hosts. INSULT™ produces circular plasmids and requires only one new primer per mutant. This obviates the need for "ultracompetent" cells, but results in entangle DNA species that decrease transformation efficiency.

The most efficient transforming species is expected to be single untangled duplexes of closed circular DNA, as plasmid preparations from E. coli culture produce. Some smaller multimers can also transform. When perfectly matched primers are designed to copy without mutation, PCR copy efficiencies of 90% per cycle are readily obtained. When mutational primers are used, PCR copy efficiency is less, and the larger the mutation attempted the smaller percentage of the DNA will be copied at each cycle. For example, with p=probability of a copy being made, and q=(1−p), the probability that a copy is not made in a particular cycle from a template molecule; after n cycles, the fraction of parental templates copied only once is $npq^{(n-1)}$, and the fraction copied twice is $\frac{1}{2} n(n-1)p^2q^{(n-1)}$. The yield of these species is very low using the INSULT® method for primer sets allowing high efficiency copying; for 80% copy efficiency, doubly copied transcripts are about 0.1% after eight cycles, and about 0.007% after ten cycles. For lower copy efficiency, the yield after eight cycles is about 3%, and after ten cycles is about 1%. Both INSULT® based products and circular PCR based protocols likely produce mutants through these low-yield pathways, enabled by low copy efficiency from primer mismatch. The yield of low complexity species from circular PCR is much lower than that obtained from INSULT® methods with any reasonable copy efficiency.

Among the transformational methods using circular DNA species, the true transforming specie is the low complexity closed circular specie but, until the present method, has been produced in low yield. The described method produced this specie in higher yield than previously possible.

The inventive method provides general approaches to result in a mutated circular deoxyribonucleotide (DNA) duplex that is substantially devoid of interlocked circular DNA. These three approaches are shown schematically in FIG. 1, and begin with a parental, fully methylated dsDNA circular duplex; methylation is shown by a short bolded solid line from a particular DNA strand. In general, a first mutagenic primer is provided under conditions to amplify the circular DNA to be mutated, resulting in a first product containing a first hemi-methylated duplex interlocked with a single stranded circular DNA. The first product is then either subjected to one of the following three approaches:

amplified using the first mutagenic primer resulting in a second product, then digesting a hemi-methylated duplex of the second product, priming with a second generic primer to form a third product, and then digesting a hemi-methylated duplex of the third product;

or the single stranded circular DNA is digested, primed with a second generic primer to form a second product containing either a single stranded circular DNA or a hemi-methylated duplex, and then digesting with either a single stranded digestion enzyme or a hemi-methylation-dependent digestion enzyme;

or amplified with a second generic primer resulting in a second product containing hemi-methylated duplexes and a unmethylated duplex, and digesting the hemi-methylated duplexes with a hemi-methylation-dependent digestion enzyme.

The end result of any approach is a mutagenic circular DNA duplex that is substantially devoid of interlocked circular DNA species.

In one embodiment, the use of digestion enzymes, e.g., ssDNA digestion enzymes or hemi-methylation-dependent digestion enzymes, is optional but may be used to increase the yield of mutagenic circular DNA duplex that is substantially devoid of interlocked circular DNA species.

Figure 1:
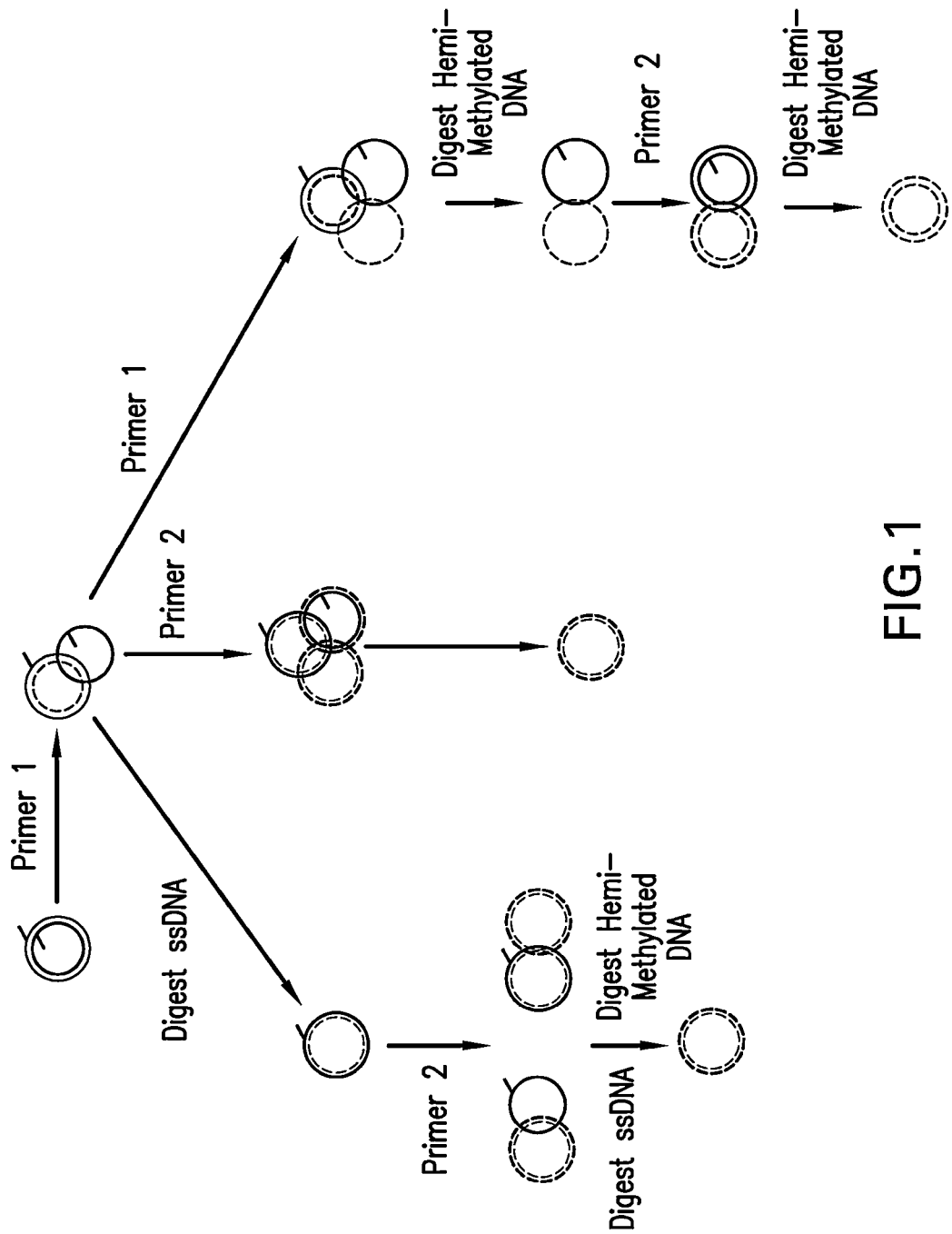
FIG. 1 shows the embodiments of the general inventive mutagenesis scheme.
Figure 2:
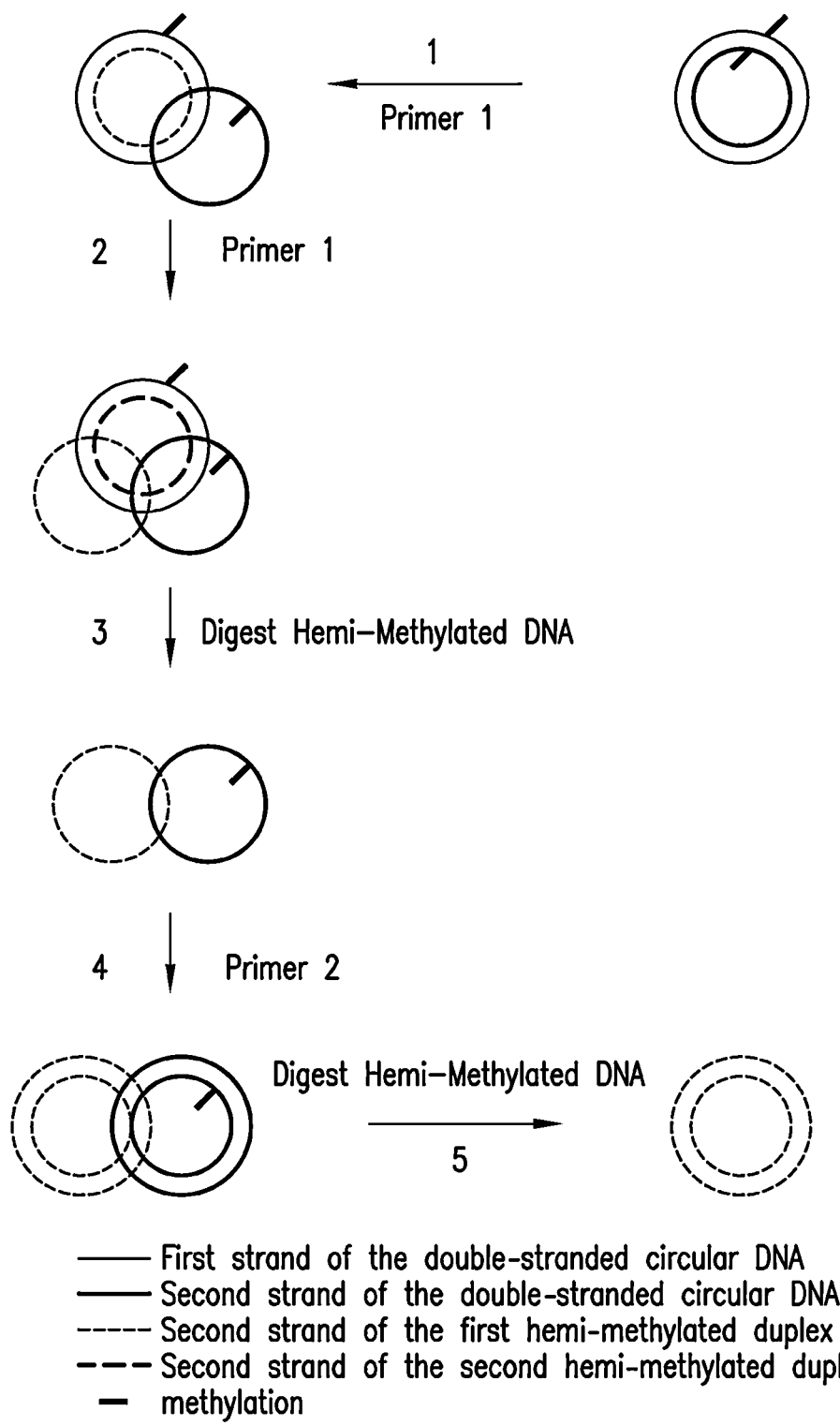
FIG. 2 shows a mutagenesis scheme according to one embodiment of the invention.
Figure 3:
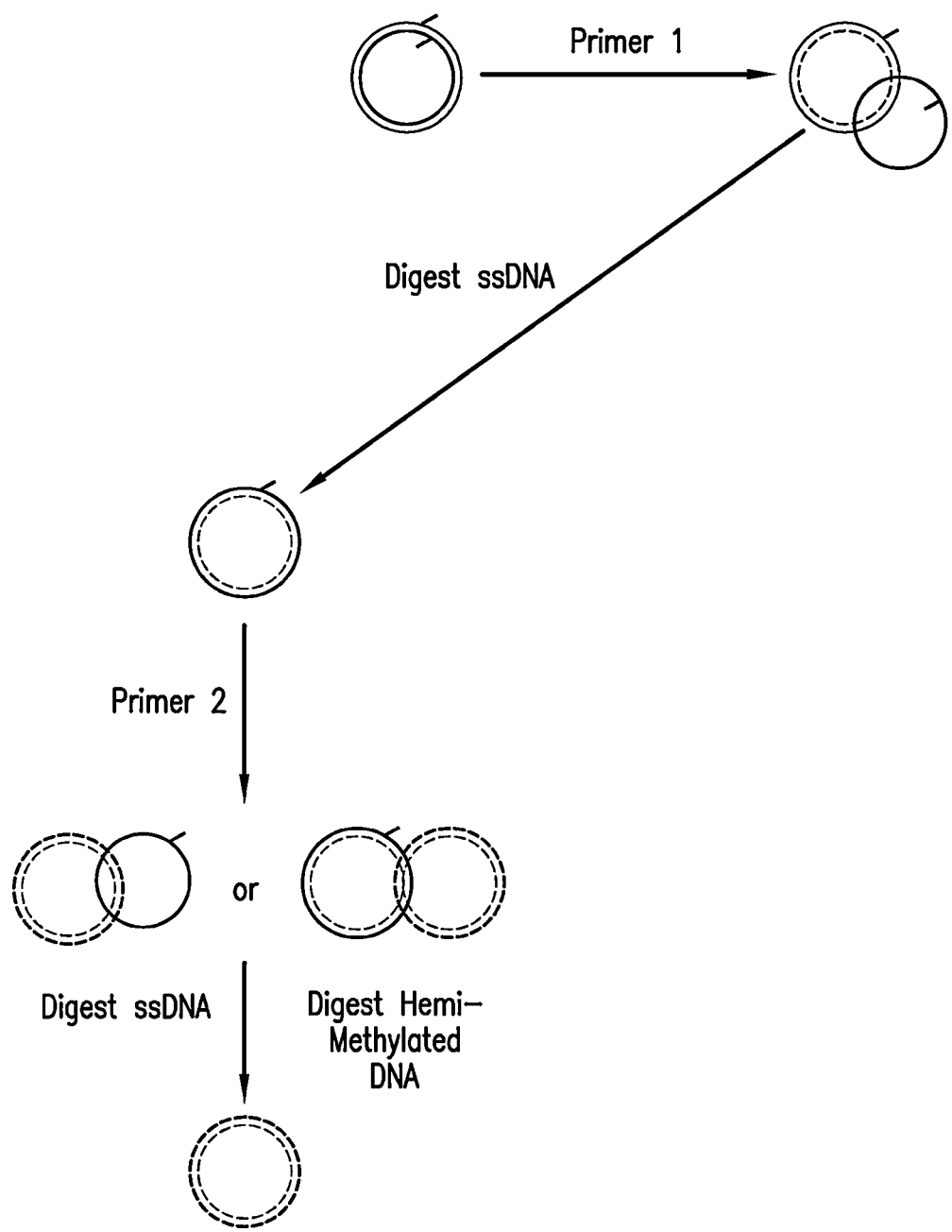
FIG. 3 shows a mutagenesis scheme according to another embodiment of the invention.
Figure 4:
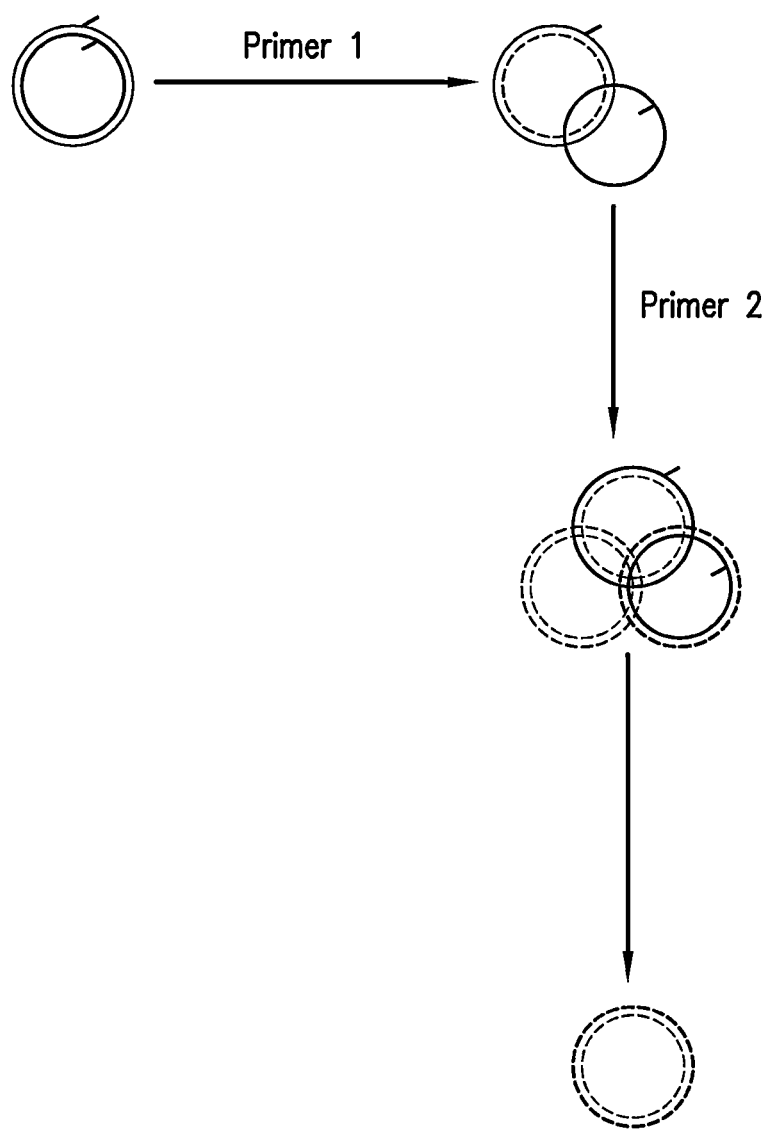
FIG. 4 shows a mutagenesis scheme according to another embodiment of the invention.

One approach, shown in FIG. 1 right side and expanded in FIG. 2, is by amplifying the DNA with a first primer, digesting the hemi-methylated product, priming with a second primer to form another product, and digesting the hemi-methylated product, resulting in a mutagenic untangled duplex DNA. Another approach, shown in FIG. 1 left side and expanded in FIG. 3, is by amplifying with a first primer, digesting single stranded circular DNA, priming with a second primer to form another product, and digesting with either a single strand digestion enzyme or an enzyme that digests both strands of a hemi-methylated duplex (a hemi-methylated-dependent digestion enzyme), resulting in a mutagenic untangled duplex DNA. Another approach, shown in FIG. 1 center and expanded in FIG. 4, is by amplifying with a first primer, then amplifying with a second primer, and digesting the hemi-methylated duplexes, resulting in a mutagenic untangled duplex DNA. One skilled in the art knows that propagating DNA in a microorganism, such as propagating a plasmid in bacteria, can result in a methylated DNA, while propagating DNA in vitro or ex vivo, e.g., using the polymerase chain reaction (PCR), results in unmethylated DNA.

The inventive method results in a low complexity DNA, a single, untangled duplex of closed circular DNA. High complexity DNA, i.e., tangled DNA, is difficult to transform. One embodiment of the method is performed as follows, and as shown schematically in FIG. 2 where the first strand of the double-stranded circular DNA is a long non-bolded solid line;
the second strand of the double-stranded circular DNA is a long bolded solid line;
the second strand of the first hemi-methylated duplex is a long non-bolded dashed line;
the second strand of the second hemi-methylated duplex is a long bolded dashed line; and methylation is a short bolded solid line:

a) starting with a double-stranded circular DNA having a methylated first strand and a methylated second strand, adding a primer (Primer 1) containing a desired mutation, i.e., a mutagenic primer, under denaturing conditions and annealing to one strand, where the first and second strands remain interlocked;

b) extending the primer with DNA polymerase, forming a first hemi-methylated product that remains interlocked with the second DNA strand, and reacting the product with a ligase forming a first hemi-methylated circular duplex that remains interlocked with the second strand;

c) after a cycle of high temperature to melt the duplexes, e.g., 95° C., repeating step (b) to extend the mutagenic primer (Primer 1), forming a second hemi-methylated product that remains interlocked with both the second strand of step (a) and the second strand of the first hemi-methylated circular duplex, and adding a ligase to form a second hemi-methylated circular duplex;

d) reacting the second hemi-methylated circular duplex with a restriction endonuclease (digest hemi-methylated DNA) under conditions that preferentially cut the duplex composed of the first strand and the second strand of the second hemi-methylated circular duplex resulting in a complex, the complex comprising two interlocked single strands: one being the methylated parental strand, and the other being the unmethylated copy formed in the first polymerase reaction;

e) adding a generic reverse primer (Primer 2) that preferentially lacks complementarity or lacks substantial complementarity with the mutagenic primer to the complex under conditions that anneal the reverse primer to the second strand of the methylated parental double-stranded circular DNA and to the second strand of the first hemi-methylated circular duplex, and extending the generic reverse primer with a polymerase to obtain a third hemi-methylated product interlocked with a first unmethylated product, and adding a ligase to complete the nicked, circular DNA; and f) reacting the third hemi-methylated product interlocked with the first unmethylated product with an enzyme (digest hemi-methylated DNA) that preferentially cuts the third hemi-methylated product, under conditions to produce a first unmethylated product without an interlocked circular DNA; and reacting the first unmethylated product without an interlocked circular DNA with a ligase under conditions to produce a first unmethylated circular duplex comprising a mutagenized circular DNA and its complementary circular DNA polynucleotide.

As shown schematically in FIG. 2, the method was initiated with a single template and a single forward mutagenic primer. The single template was a double-stranded circular DNA that has a methylated first strand and a methylated second strand. The primer contained the desired mutation to be propagated, i.e., it was a mutagenic primer, defined as a primer with at least one intentional mismatch. The mismatch is at least one of a base substitution, base insertion, and/or base deletion. The primer was added to the template under denaturing conditions causing the first strand to interlock with the second strand and to anneal the primer to only the first DNA strand. The primer was extended by adding a polymerase, forming a first hemi-methylated product that remained interlocked with the second DNA strand, then the product was filled by reacting the product with a ligase forming a first hemi-methylated circular duplex that remained interlocked with the second strand (step 1). In one embodiment, the ligase and/or the polymerase was/were thermostable, making it/them suitable for use in the polymerase chain reaction (PCR). In one embodiment, non-thermostable enzymes were used, and were renewed as needed, as known by one skilled in the art, after the temperature was raised to break the DNA duplexes.

In step 2 of FIG. 2, the same primer as in step 1 was used, under the same conditions of step 1, to the first hemi-methylated circular duplex. The same polymerase as is step 1 was added to extend the primer, forming a second hemi-methylated product that remained entangled with both the second strand, and the second strand of the first hemi-methylated circular duplex. A ligase was then added to form a second hemi-methylated circular duplex, an entangled unmethylated mutant strand, and a second strand of the double-stranded circular DNA. Thus, after the first cycle, the successful copies are a hemi-methylated duplex in which the unmethylated strand is mutagenized; this is entangled with a methylated parental single strand. The second cycle displaced the mutant strand and synthesized a second mutant copy. The new hemi-methylated duplex was now entangled with both the parental single strand and the mutant single strand produced in the first cycle.

In step 3 of FIG. 2, the second hemi-methylated circular duplex was digested by reacting it with an enzyme, e.g., a restriction endonuclease, under conditions that preferentially cut the first strand and the second strand, resulting in a complex. The complex contained the second strand of the methylated double-stranded circular DNA entangled with the second strand of the first hemi-methylated circular duplex. This step simplified the system, i.e., it decreased the complexity of the complex, leaving two entangled strands. An enzyme that recognized a methylated sequence (added by, e.g., dAM or dCM) e.g., dpn1, untangled the hemi-methylated strand from the single stranded product, i.e., this was targeted untangling. In one embodiment, it used a restriction enzyme such as dpn1. Dpn1 digests hemi-methylated DNA with lower activity than fully methylated DNA, so it is desirable to inactivate the ligase before digestion to ensure that the cuts are not rapidly repaired. The remaining product was a single closed circular unmethylated strand topologically entangled with a single close circular parental methylated strand. The methylated strand had not been digested because dpn1 does not recognize single stranded DNA. Alternatively, an enzyme specific for double stranded DNA can be used.

In step 4 of FIG. 2, reverse generic primer was added under conditions that annealed the reverse primer to the second strand of the methylated double-stranded circular DNA and to the second strand of the first hemi-methylated circular duplex, and extended the generic reverse primer with a polymerase to obtain a third hemi-methylated product entangled with a first unmethylated product. The reverse generic primer enabled the next cycle to synthesize complements to both the remaining single strands, and allowed synthesis of new reverse strands.

In step 5 of FIG. 2, the third hemi-methylated duplex entangled with the first unmethylated product was reacted with an enzyme that preferentially cut the third hemi-methylated product. The enzyme may be a restriction endonuclease, e.g., dpn1 or other nuclease. Alternative enzymes and sequences are possible as described and as known by one skilled in the art. For example, WO 2005-040342 discloses a method to cleave RNA/DNA duplexes by restriction enzymes, and to identify appropriate enzymes for that purpose. That method includes combining a restriction endonuclease, isochizomer or modification thereof, with an RNA/DNA duplex in a mixture, where the restriction endonuclease, isoschizomer or modification thereof is capable of cleaving the RNA/DNA duplex to form a plurality of RNA/DNA duplex fragments of specific sizes with defined ends, and cleaving the RNA/DNA duplex. Restriction endonucleases that may be used in that method include, e.g., Avall, Cac8l, Bstl, SfaNl, and Sau3Al. Sau3Al is an example of a restriction endonuclease that does not require modification to cleave only RNA. Other examples of restriction endonucleases are available (New England Biolabs catalog (Beverly Mass.), in REBASE@, in Roberts et al. Nucleic Acids Res. 31: 418 (2003)). In WO 2005/040342, the substrates used in the examples are short duplexes prepared by annealing a synthetic ribo-oligonucleotide (RNA strand) with a synthetic deoxyribo-oligonucleotide (DNA strand) (Example 1). Alternatively, metal ions other than magnesium can be included in the mixture for inhibiting DNA duplex cleavage by the restriction endonuclease.

The step 5 reaction was performed under conditions to produce a first unmethylated product without an entangled circular DNA. The first unmethylated product without an interlocked circular DNA was then reacted with a ligase. The final product was a first unmethylated circular duplex containing a mutagenized circular DNA, i.e., a single un-nicked unmethylated closed circular duplex with both strands mutated, and its complementary circular DNA.

One embodiment of the method is performed as follows, and as shown schematically in FIG. 3, where the first strand of the double-stranded circular DNA is a long non-bolded solid line; the second strand of the double-stranded circular DNA is a long bolded solid line; the second strand of the first hemi-methylated duplex is a long non-bolded dashed line; the first strand of the first unmethylated circular duplex is a long bolded dashed line; and methylation is a short bolded solid line:

a) starting with a double-stranded circular DNA having a methylated first strand (solid line) and a methylated second strand (solid bold line), adding a first primer (Primer 1) containing a desired mutation under denaturing conditions such that the primer anneals to one strand;

b) extending the primer with DNA polymerase, forming a first hemi-methylated product containing the methylated first strand (solid line) and second strand of the first hemi-methylated duplex (dashed line) that remains interlocked with the second DNA strand (solid bold line), and reacting the product with a ligase forming a first hemi-methylated circular duplex that remains interlocked with the second strand;

c) reacting the single parental methylated circular duplex with a restriction endonuclease (digest ssDNA) under conditions that preferentially cut single stranded DNA of the methylated second strand (solid bold line);

d) adding a generic reverse second primer (Primer 2) that preferentially lacks complementarity or lacks substantial complementarity with the mutagenic primer to the complex under conditions that anneal the reverse primer to the unmethylated second strand of the first hemi-methylated duplex (dashed line) single stranded circular DNA producing an unmethylated nicked duplex (dashed line duplex), entangled with the methylated first strand (solid line), and closing the nick with a ligase; (if the first primer is still present, the product may also include a hemi-methylated duplex (solid line/dashed line duplex) entangled with the unmethylated nicked duplex); and f) reacting the product with an enzyme that preferentially cuts either the methylated first strand (solid line) single stranded DNA (digest ssDNA) or, if the initial primer is still present, cuts the hemi-methylated duplex DNA (solid line/dashed line duplex)(digest hemi-methylated DNA), under conditions to produce unmethylated duplex product (dashed line duplex) without an interlocked circular DNA; and reacting the first unmethylated product without an interlocked circular DNA with a ligase under conditions to produce a first unmethylated circular duplex comprising a mutagenized circular DNA and its complementary circular DNA polynucleotide.

One embodiment of the method is performed as follows, and as shown schematically in FIG. 4 where the first strand of the double-stranded circular DNA is a long non-bolded solid line; the second strand of the double-stranded circular DNA is a long bolded solid line; the second strand of the first hemi-methylated duplex is a long non-bolded dashed line; the first strand of the first unmethylated circular duplex and the second hemi-methylated duplex is a long bolded dashed line; and methylation is a short bolded solid line:

a) starting with a double-stranded circular DNA having a methylated first strand (solid line) and a methylated second strand (solid bold line), adding a first primer (Primer 1) containing a desired mutation under denaturing conditions such that the primer anneals to one strand;

b) extending the primer with DNA polymerase, forming a first hemi-methylated product containing the methylated first strand (solid line) and second strand of the first hemi-methylated duplex (dashed line) that remains interlocked with the second DNA strand (solid bold line), and reacting the product with a ligase forming a first hemi-methylated circular duplex that remains interlocked with the second strand;

c) adding a second generic primer (Primer 2), and after a cycle of high temperature to melt the duplexes, e.g., about 95° C., repeating step (b) to extend the first and second primers, forming two additional hemi-methylated products (solid line/dashed line duplex and solid bold line/dashed bold line duplex) that are entangled with each other and with an unmethylated duplex (dashed line/dashed bold line duplex) formed simultaneously, with all three nicked duplexes sealed by ligase; and d) reacting the complex with a restriction endonuclease (digest hemi-methylated DNA) under conditions that preferentially cut the hemi-methylated duplexes (solid line/dashed line duplex and solid bold line/dashed bold line duplex) to produce an unmethylated circular duplex (dashed line/dashed bold line duplex) comprising a mutagenized circular DNA and its complementary circular DNA polynucleotide.

The unmethylated closed circular mutant duplex was an ideal transforming species.

Multiple mutations were introduced simultaneously using multiple mutagenic primers.

Alternative strategies are available to untangle the entangled DNA. As one example, primers may be varied during the first two cycles to remove selected restriction sites. As one example, primers may be varied during the first two cycles to insert selected restriction sites, where these created restriction sites could be digested by a selected restriction endonuclease, to result in untangled, circular DNA. As one example, a strand number based strategy is simple, workable, and is based on the fact that S1 type nucleases digest only single stranded DNA. Digestion with a single strand specific nuclease after the first cycle leaves only the hemi-methylated duplex. After the second cycle, digestion with any suitable nuclease with double stranded specificity leaves only the single stranded unmethylated mutant strand produced in the first cycle. Addition of the second primer now allows synthesis of a clean mutant closed circular duplex.

The topoisomerase II enzyme untangles plasmid DNA during normal replication. In principle, topoisomerase II can be used to simplify concatamers formed during INSULT type linear amplification or circular PCR. However, topoisomerase II does not 'untie' DNA; it merely allows one duplex to pass through another. If the local DNA concentration is not very high, this process will favor deconcatenation, but the rate may be too low to be practically useful in the absence of a force that physically separates the entangled strands. Large concatamers may not be simplified using topoisomerase II, but topoisomerase II deconcatenation may be used with SIMPLEX variants in which extra cycles are added to increase the yield from primers with extensive mismatches.

Some mutations are simple 1 to 3 base substitutions. For these mutations, in most cases, primers can be designed to produce reasonable copy efficiency. It is often desirable to produce extensive modifications, including many base deletions and/or many base insertions. These primers sets are of much lower efficiency.

Using the previous p=probability of a copy being made, and q=(1−p) the probability that a copy is not made in a particular cycle from a template molecule the fraction of templates copied twice is just $\frac{1}{2}n(n-1)p^2q^{(n-1)}$. The special significance of doubly copied template is that this is the form most readily converted to single duplex closed circular mutant. Extra copies are not readily de-concatenated because they are identical; production of unconcatenated duplexes must rely on partial activity.

Using the Insult method, it is suggested that the method should be performed with additional cycles for difficult mutation targets. However, using the inventive present method, large numbers of copies were not required for transformation, because cells were transformed in high yields even when only small amounts of the mutagenic plasmids were applied. For many mutagenic vectors, only a small fraction of the respective vector samples have been able to enter the cell.

In one embodiment, a plurality of mutations can be introduced simultaneously by using more than one sequence of mutagenic primers. The segments produced during the first two cycles are then connected by ligase-mediated reactions at the same time as the nick is closed in single mutagenic primer methods.

In one embodiment, the method comprises amplification under PCR conditions, e.g., about 35 cycles, with a thermostable polymerase, e.g., Taq or Pfu, producing ~1 copy from paternal strands per cycle. The primers are not complementary, and are separated, e.g., by a few hundred to about 2000 base pairs. After the first cycle, PCR amplification of the region between the two primers begins, but does not produce a suitable transforming species. After a few cycles, full length linear copies form closed nicked circles with short copies, which are extended by the polymerase to produce full length mutagenic copies, which are potential transformants. This amplification is not exponential, but is faster than linear growth. Next, the nicked circular products may be ligated, which improves transformation.

The method benefits from additional cycles for some mutation targets defined generally as difficult mutations.

Figure 5A:
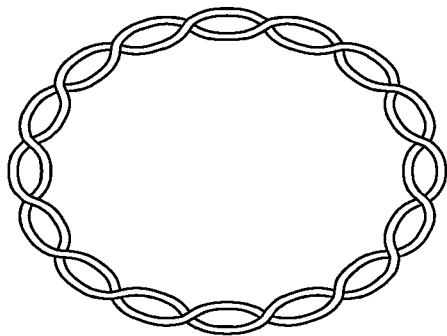
FIG. 5 shows topology of circular DNA.
Figure 5B:
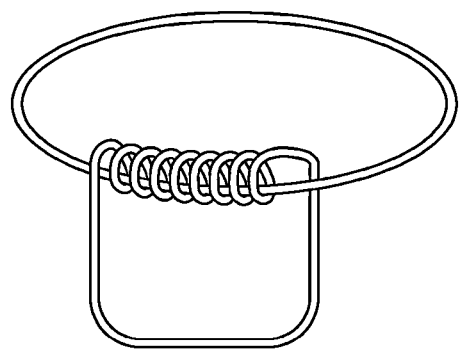

FIG. 5 shows a schematic of non-denatured DNA duplex (FIG. 5A) and a melted or denatured DNA duplex (FIG. 5B) where melting of the duplex breaks hydrogen bonds between complementary strands, but the two single stranded circular DNA strands remain topologically concatenated and cannot be separated without breaking at least one of the strands. While the schematic shows about 10 turns of one DNA strand wrapped around another, in practice, a DNA plasmid would have hundreds, and perhaps thousands, of turns of one DNA strand around another.

Figure 6:
FIG. 6 models topological concatenation of amplifying DNA having a closed, double helical, conformation.

FIG. 6 shows a paper model of hairball formation by DNA copying. The model is a duplex with only two full turns, while actual plasmids have thousands of turns, resulting in more complex concatenation. A single closed plasmid is represented in the upper left. Moving clockwise, a single copy cycle produces a topologically concatenated duplex-duplex (two primers) or duplex-single stranded pair. The structure at the lower left results after two copy cycles with two primers. These data indicate that circular PCR is not practical; it produces few copies, not exponential amplification.

Figure 7:
FIG. 7 is a photograph of an agar plate showing growth of bacterial colonies transformed with mutated DNA created using one embodiment of the method.

FIG. 7 is a photograph of an agar plate showing growth of bacterial colonies transformed with mutated DNA created using one embodiment of the method. A mutation was created in the β-galactosidase gene (β-gal), and then was used to transform chemically-competent bacterial cells, e.g., non-ultra-competent bacterial cells. The template for the mutagenesis was pGEM-3Zf(+) (Promega). The mutagenic primer created a single point mutation (T to a G at position 3183) incorporating an amber stop codon about one third into the β-galactosidase gene. The reverse primer, complementary to the opposite strand as the mutagenic primer, begins at position 2917 in the plasmid. The primers were 5'-phosphorylated to enable ligation. The mutagenic primer, pGEM-Amber3183, begins at position 3169 of plasmid, and the non-mutagenic primer pGEM-Rev2917, begins at position 2917 of plasmid. The PCR amplification used Q5 polymerase (NEB), following their standard protocol, using an annealing temperature of 69° C. Reactions were purified using Zymo Research DNA Clean & Concentrator kit, and ligations were performed with T4 DNA ligase (NEB). Both ligated and unligated PCR product were transformed into DH5α cells prepared with a procedure adapted from Chung and Miller, Nucleic Acid Research 16 #8, 1988. Ligation of the PCR products greatly enhanced the number of mutants seen on the plate.

The transformed cells were plated on an agar plate containing X-gal and incubated. As shown in FIG. 7, a large number, about 3-4:1, of the bacterial colonies were white, e.g., did not produce the characteristic blue colonies (shown as dark grey in FIG. 7) which result from expression of a functional β-gal gene, indicating that most of the colonies contained mutant β-gal. In contrast, existing mutagenesis kits are unable to result in mutant colonies using non-ultra-competent cells (data not shown). The inventive method resulted in transformation and growth of a large percentage of mutant colonies even using non-ultra-competent cells.

The embodiments shown and described in the specification are only specific embodiments of inventors who are skilled in the art and are not limiting in any way. Therefore, various changes, modifications, or alterations to those embodiments may be made without departing from the spirit of the invention in the scope of the following claims. The references cited are expressly incorporated by reference herein in their entirety.

What is claimed is:

1. A method to create a mutated circular deoxyribonucleotide (DNA) duplex substantially devoid of interlocked circular DNA species, the method comprising
providing a mutagenic primer under conditions to amplify the circular DNA to be mutated, resulting in a first product containing a first hemi-methylated duplex interlocked with a single stranded circular DNA, and thereafter
(i) amplifying the first product using the mutagenic primer resulting in a second product, digesting a hemi-methylated duplex of the second product, priming with a generic primer to form a third product, and then digesting a hemi-methylated duplex of the third product;
or
(ii) digesting the single stranded circular DNA, priming with a generic primer to form a second product containing either a single stranded circular DNA or a hemi-methylated duplex, and then digesting with either a single stranded digestion enzyme or a hemi-methylation-dependent digestion enzyme;
or
(iii) amplifying the first product with a generic primer resulting in a second product containing hemi-methylated duplexes and an unmethylated duplex, and digesting the hemi-methylated duplexes with a hemi-methylation-dependent digestion enzyme,
the method resulting in a mutagenic circular DNA duplex substantially devoid of interlocked circular DNA species.

2. The method of claim 1 further comprising transforming a microorganism with the resulting mutagenic circular DNA duplex substantially devoid of interlocked circular DNA species.

3. A method to mutate a circular deoxyribonucleotide (DNA), the method comprising
(a) providing a double-stranded circular DNA having a methylated first strand and a methylated second strand,
(b) adding a mutagenic primer containing a desired mutation under denaturing conditions and annealing to one strand, where the first and second strands are interlocked,
(c) extending the mutagenic primer with a DNA polymerase, forming a first hemi-methylated product that remains interlocked with the second DNA strand, and reacting the product with a ligase forming a first hemi-methylated circular duplex interlocked with the second strand;
(d) denaturing the product of step (c) then repeating step (c) on the denatured product to extend the mutagenic primer, resulting in a second hemi-methylated product interlocked with both the second strand from step (b) and the second strand of the first hemi-methylated circular duplex from step (c), and adding a ligase to form a second hemi-methylated circular duplex;
(e) reacting the second hemi-methylated circular duplex of step (d) with a restriction endonuclease under conditions that preferentially digest the duplex composed of the first strand and the second strand of the second hemi-methylated circular duplex resulting in a complex, the complex comprising two interlocked single strands of one methylated parent strand and one unmethylated copy resulting from the first polymerase reaction;
(f) adding a generic reverse primer that lacks complementarity or lacks substantial complementarity with the mutagenic first primer to the complex under conditions that anneal the reverse primer to the second strand of the methylated parent double-stranded circular DNA and to the second strand of the first hemi-methylated circular duplex, and extending the generic reverse primer with a DNA polymerase to obtain a third hemi-methylated product interlocked with a first unmethylated product, and adding a ligase to complete the nicked, circular DNA;
(g) reacting the third hemi-methylated product interlocked with the first unmethylated product with an enzyme that preferentially cuts the third hemi-methylated product, under conditions to produce a first unmethylated product without an interlocked circular DNA; and reacting the first unmethylated product without an interlocked circular DNA with a ligase under conditions to produce a first unmethylated circular duplex comprising a mutagenized circular DNA and its complementary circular DNA polynucleotide,
resulting in a mutagenized circular duplex DNA substantially free of additional entangled circular DNA species.

4. The method of claim 3 further comprising transforming a microorganism with a composition comprising the product of step (g) which is a first unmethylated circular duplex.

5. The method of claim 3 wherein low complexity of the first unmethylated circular duplex provides an efficiency of the transformation.

6. The method of claim 3 wherein the enzyme is a methylation-dependent restriction endonuclease.

7. The method of claim 6 wherein the methylation-dependent endonuclease is DpnI.

8. The method of claim 3 wherein the method does not amplify the methylated double-stranded circular DNA starting material.

9. The method of claim 3 wherein the mutagenic primer inserts at least one nucleotide into the methylated double-stranded circular DNA, deletes at least one nucleotide from the methylated double-stranded circular DNA, and/or substitutes at least one nucleotide of the methylated double-stranded circular DNA.

10. The method of claim 3 further comprising repeating steps (a) through (g) at least once.

11. The method of claim 4, where transforming is performed in the absence of ultracompetent microorganisms.

12. The method of claim 3 wherein the DNA polymerase is thermostable or non-thermostable.

13. The method of claim 12 wherein the DNA polymerase is a non-thermostable polymerase and is renewed as needed at each of steps (c), (d) and (f).

14. The method of claim 3 further comprising at least two mutagenized primers.

15. The method of claim 3, further comprising, prior to step a), subcloning a DNA to be mutated into a suitable vector and propagating the vector to result in a methylated DNA-containing vector.

16. A method to mutate a circular deoxyribonucleotide (DNA), the method comprising
a) starting with a double-stranded circular DNA having a methylated first strand and a methylated second strand, adding a primer containing a desired mutation under denaturing conditions such that the primer anneals to one strand;

b) extending the primer with DNA polymerase, forming a first hemi-methylated product that remains interlocked with the second DNA strand, and reacting the product with a ligase forming a first hemi-methylated circular duplex that remains interlocked with the second strand;

c) reacting the single parental methylated circular duplex with a restriction endonuclease under conditions that preferentially cut single stranded DNA;

d) adding a generic reverse primer that preferentially lacks complementarity or lacks substantial complementarity with the mutagenic primer to the complex under conditions that anneal the reverse primer to the unmethylated single stranded circular DNA producing an unmethylated nicked duplex, entangled with a single methylated strand, and adding a ligase to complete the circular DNA; and f) reacting the product with an enzyme that preferentially cuts either single stranded DNA or, if the initial primer is still present, hemi-methylated duplex DNA, under conditions to produce unmethylated duplex product without an interlocked circular DNA; and reacting the first unmethylated product without an interlocked circular DNA with a ligase under conditions to produce a first unmethylated circular duplex comprising a mutagenized circular DNA and its complementary circular DNA polynucleotide.

17. A method to mutate a circular deoxyribonucleotide (DNA), the method comprising a) starting with a double-stranded circular DNA having a methylated first strand and a methylated second strand, adding a primer containing a desired mutation under denaturing conditions such that the primer anneals to one strand;

b) extending the primer with DNA polymerase, forming a first hemi-methylated product that remains interlocked with the second DNA strand, and reacting the product with a ligase forming a first hemi-methylated circular duplex that remains interlocked with the second strand;

c) adding a second generic primer, and after a cycle of high temperature to melt the duplexes, repeating step (b) to extend the primers, forming two additional hemi-methylated products that are entangled with each other and with an unmethylated duplex formed simultaneously, with all three nicked duplexes sealed by ligase; and d) reacting the second hemi-methylated circular duplex with a restriction endonuclease under conditions that preferentially cut the hemi-methylated duplexes to produce an unmethylated circular duplex comprising a mutagenized circular DNA and its complementary circular DNA polynucleotide.

* * * * *